United States Patent [19]
Schreiber et al.

[11] Patent Number: 5,645,798
[45] Date of Patent: Jul. 8, 1997

[54] TEST ELEMENTS IN SEALED CHAMBERS FOR ANALYZING COMPOUNDS CONTAINED IN LIQUID SAMPLES

[75] Inventors: Joerg Schreiber, Heddesheim; Wilfried Schmid; Hans-Juergen Kuhr, both of Mannheim; Heino Eikmeier, Zvewegemer; Klaus-Dieter Sacherer, Kirchheim, all of Germany

[73] Assignee: Boehringer Mannheim GmbH, Mannehim, Germany

[21] Appl. No.: 464,405

[22] Filed: Jun. 5, 1995

Related U.S. Application Data

[62] Division of Ser. No. 231,712, Apr. 22, 1994, Pat. No. 5,489,414.

[30] Foreign Application Priority Data

Apr. 23, 1993 [DE] Germany .......... 43 13 252.9
Aug. 27, 1993 [DE] Germany .......... 43 28 816.2

[51] Int. Cl.$^6$ .................................. G01N 35/10
[52] U.S. Cl. .................. 422/58; 422/63; 422/64; 422/104; 436/43; 436/46; 436/164
[58] Field of Search ............... 422/55, 58, 63, 422/64, 66, 65, 99, 104; 436/43, 44, 46, 164, 805, 810; 435/805, 808

[56] References Cited

U.S. PATENT DOCUMENTS

| | | |
|---|---|---|
| 3,651,927 | 3/1972 | Richardson et al. . |
| 3,932,133 | 1/1976 | Ishikawa .................... 422/65 |
| 4,218,421 | 8/1980 | Mack, Jr. et al. .......... 422/66 |
| 4,301,414 | 11/1981 | Hill et al. .................. 324/446 |
| 4,328,184 | 5/1982 | Kondo ........................ 422/58 |
| 4,751,184 | 6/1988 | Higo et al. . |
| 4,798,705 | 1/1989 | Jakubowicz et al. . |
| 4,855,109 | 8/1989 | Muraishi et al. . |
| 4,857,272 | 8/1989 | Sugaya ........................ 422/65 |

(List continued on next page.)

FOREIGN PATENT DOCUMENTS

| | | |
|---|---|---|
| 0150965 | 8/1985 | European Pat. Off. . |
| 0377503 | 7/1990 | European Pat. Off. . |
| 80331 | 3/1963 | France . |
| 2361651 | 3/1978 | France . |
| 2476350 | 8/1981 | France . |
| 4035052 | 6/1991 | Germany . |
| 60-57259 | 4/1985 | Japan . |
| 6057259 | 4/1985 | Japan . |
| 258105 | 9/1926 | United Kingdom . |
| WO-A-9302364 | 2/1993 | WIPO . |
| WO-A-9201780 | 1/1994 | WIPO . |

OTHER PUBLICATIONS

Patent Abstracts of Japan, vol. 8, No. 129, Jun. 15, 1984, JP-A-59 032 851.
Patent Abstracts of Japan, vol. 7, No. 172, Jul. 29, 1983, JP-A-58 077 663.
Patent Abstracts of Japan, vol. 9, No. 40, Feb. 20, 1985, JP-A-59 180 461.
Patent Abstracts of Japan, vol. 10, No. 177, Jun. 21, 1986, JP-A-61 026 864.
Patent Abstracts of Japan, vol. 9, No. 182, Jul. 27, 1985, JP-A-60 055 264.
Patent Abstracts of Japan, vol. 10, No. 67, Mar. 15, 1986, JP-A-60 207 598.

*Primary Examiner*—Long V. Le
*Attorney, Agent, or Firm*—Nikaido, Marmelstein, Murray & Oram LLP

[57] ABSTRACT

A system for analyzing sample liquids using dry reagents which is particularly suitable for the determination of clinical parameters. The system includes an analysis instrument containing the individually sealed test elements to carry out an analytical test. Shape and nature of the test elements were designed to match the analysis system. The system is particularly suitable for analyses where the available test elements exhibit a low storage stability when brought into contact with the environment.

11 Claims, 4 Drawing Sheets

U.S. PATENT DOCUMENTS

| | | |
|---|---|---|
| 4,948,737 | 8/1990 | Quenin et al. . |
| 5,075,079 | 12/1991 | Kerr et al. ............................... 422/64 |
| 5,089,418 | 2/1992 | Shaw et al. . |
| 5,102,624 | 4/1992 | Muraishi . |
| 5,154,889 | 10/1992 | Muraishi . |
| 5,167,922 | 12/1992 | Long . |
| 5,219,526 | 6/1993 | Long . |
| 5,270,006 | 12/1993 | Uchigaki et al. . |
| 5,332,549 | 7/1994 | MacIndoe, Jr. . |

TEST ELEMENTS IN SEALED CHAMBERS FOR ANALYZING COMPOUNDS CONTAINED IN LIQUID SAMPLES

This is a division of application Ser. No. 08/231,712; filed Apr. 22, 1994, now U.S. Pat. No. 5,489,414.

TECHNICAL FIELD

The invention addresses a system for analyzing sample liquids, said system comprising a mechanical device for transporting test elements, a measuring arrangement for detecting changes occurring on a test element and two or more individually sealed test elements included within said system. Further, the invention addresses the actual test elements, a mechanically linked arrangement of said test elements and a method of analyzing sample liquids.

BACKGROUND OF THE INVENTION

Systems which allow an analysis without handling liquid reagents are primarily used in the fields of medicine and environmental analysis. They are referred to as dry tests. With these systems, the user can carry out analytical tests for individual parameters without having the necessary scientific background in chemistry or biochemistry. If all instructions are carried out properly, the measurements will be exact. Such systems can, hence, be used by untrained personnel, and are consequently of particular significance in the medical field when Used by patients.

In the last years, instruments for monitoring blood glucose levels by the patients have gained more and more importance. The use of instruments which can be carried along at any time makes the patient largely independent of the treating physician and, hence, increases the patient's quality of life. The option of simple and fast measurement improves drug administration, e.g. stabilization of the blood glucose level by administering insulin or sugar corresponding to the organism's requirement. Even the patient's way of living can thus be adjusted to the actual needs of the body. In the future, portable patient-operated instruments will also be employed for the determination of other blood components. In addition to endogenous substances, this includes the monitoring of drug concentrations in the blood. Such monitoring gains particular importance if the pharmacological spectrum of a therapeutic agent is narrow, as it is the case with digitalis steroids or lithium, for example.

In currently known embodiments of instruments for measuring the components of body fluids, instrument and test reagents are separated. The test reagents are available, for example, in the form of test strips onto which the body fluid is applied. The test strip is then inserted into the instrument for measurement. The storage stability of many reagents is drastically reduced by moisture. A known possibility of ensuring the storage stability of test elements over a longer period of time is to seal them in metal foil. This is usually done with urine test strips, for example. Another possibility of storing moisture-sensitive reagents is to store a great number of test elements in containers, i.e. usually vials which are made of a material that is impermeable to humidity. The test elements can then be individually removed from these containers. When the containers are opened, however, moisture can enter together with the ambient air. In order to ensure a certain storage stability of the remaining test elements, a drying agent to absorb any moisture that may have entered is provided inside the container. The user must, hence, carry a separate supply of test elements in addition to the instrument.

A procedure for analyzing a sample liquid known in prior art, for example for the determination of glucose in blood, comprises the following operating steps:

Manual removal of a test strip from a separate storage container

Application of the sample liquid

Inserting a test element into the instrument

Carrying out the measurement

Reading off the measurement value

Discarding the used test element.

The above-mentioned precautions against humidity must already be taken when removing a test element from a separate container. Further, the test strip may be contaminated by did adhering to the hands which could ultimately lead to false test results. Another source of contamination of the test strip is by accidentally dropping it. The following steps of sample application and insertion into the instrument are switched in some prior art instruments. In these cases, sample application is carried out while the test element is already in the instrument. This facilitates, for example, application of a blood droplet from the tip of a finger, which has been pricked with a lancet, as the test element is fixed in its position by the instrument.

In known analysis systems where individual test elements are employed, the user manually moves such an element to the site of measurement. In order to avoid errors due to incorrect positioning, the instrument must be given a corresponding structural design. Test elements in the form of a strip, for example, are inserted into a given guide element until contact is made with an abutment.

Analysis can be accomplished by a way of detectable signals whose strength depends on the concentration of the parameter to be determined in the sample. The expert is familiar with detectable signals that are suitable for such analyses, e.g. optical, electrical, or magnetic signals.

In instruments for use with test elements, the measurement is usually carried out by means of reflectance photometry. Less used instruments are those which employ transparent test elements where the detection is quantified in terms of the transmission. The measurements are evaluated with electronic and usually also digital means.

Analysis instruments containing a multitude of test strips have so far been limited to laboratories or larger physicians' offices as these places achieve a high throughput of individual tests rendering additional precautions against humidity and the influence of light superfluous. Patent application EP-A-0513618, for example, describes a radial arrangement of test elements. The test elements are removed from the arrangement by means of a mechanical device and the sample liquid is applied by means of a pipette. As opposed to the present invention, the test elements are not sealed inside the instrument. This arrangement was, therefore, designed to use all test elements within a short time, usually minutes or hours.

SUMMARY OF THE INVENTION

It was an object of the invention to provide an analysis system where several test elements are provided within the system such that a high storage stability of test elements is ensured even when the elements are removed individually.

A system for analyzing sample liquids was, hence, designed which features a mechanical device for transporting the test elements to the site of measurement and a measuring arrangment for detecting changes occurring on the test elements and where two or more individually sealed test elements are provided within the system. The invention also covers a mechanically linked arrangement of individually sealed test elements. The test elements as such are also part of the invention, as their design renders them particularly suitable for use in the system of the invention.

The invention further covers a system for analyzing sample liquids which makes use of the system of the invention.

A system in accordance with the invention comprises a measuring instrument and an arrangement of test elements.

The present invention focuses in particular on the test elements which are considered a part of the system. They are provided with a base made of a mechanically stable material, preferably plastic. Metal, glass, or cardboard are, however, also possible materials. The base is preferably a flat body containing a test field in a recess. Possible test fields can consist of several layers. In addition to a layer where a detectable signal is generated with the aid of the analyte and the reagents, one also knows layers which contain auxiliary substances or serve to separate cells. A possible structural design of a test field is described in patent application EP-A-0271854. In a test element according to the invention, the test field can be attached, for example, by gluing or pressing it into the base. On the one side of the test field, preferably the upper side, a liquid analyte can be applied. The analyte penetrates into the test field resulting in the separation of cells, for example, and/or initiating a reaction with several auxiliary substances, if necessary. In one of the possible layers, preferably the one located at the lower side of the test element, a detectable change is triggered in dependency upon the analyte. Preferably, these detectable changes are color changes, but other detectable properties, such as change of the magnetic or electric properties or the emission of light are also possible. The shape of the test elements also depends on the test layers necessary for the detection. However, those preferred test elements are those which can be moved or pressed out of their sealed wrapping due to their mechanical stability and/or form. For the same reasons, preferred test elements are those that have a tip or edge, particularly preferred in one direction of transportation. Moreover, preferred embodiments of the test elements are provided with guiding elements, which facilitate transportation to the site of measurement. Further, preferred embodiments of test elements have a contact point for a transportation mechanism.

Principally, the expert can detect changes on the test element by way of known measurement arrangements comprising a radiation source and a radiation detector. The radiation used for the measurement is preferably within the visible range of the frequency spectrum. In the preferred case that a reflectance arrangement has been selected, the radiation emitted by the source arrives at the lower side of the test field where the beams are reflected either directly or after traversing an optical unit. The reflected beams then arrive at the receiver either directly or after traversing an optical unit. The receiver can be a photodiode, for example a photomultiplier or a photovoltaic element. The above-mentioned optical unit can comprise optical lenses and mirrors. Moreover, diffraction grids, prisms, and optical filters which select a desired small frequency range out of the larger frequency range of the available spectrum are also used. Further, it is possible to employ measurement arrangements where the above described selection of a small frequency range is realized after being reflected by the test element, but prior to entering the receiver. Evaluation of the arriving radiation is carried out in a known way by means of an electronic circuit and the result is then displayed. With a suitable receiver, it is also possible to show the signal directly on a display. The display can, for example, be an analog display, preferably it is a digital display.

The invention further addresses a mechanically linked arrangement of test elements, characterized in that each test element contained therein is individually sealed. Individually sealed refers to the air- and water-tight separation of individual test elements with respect to the environment outside the sealing and with respect to each other. The test elements of this arrangement correspond to the above-described test elements of the invention. A separate sealing of each individual element is preferably realized by sealing the test elements in blister packs. A particularly preferred arrangement is a radial arrangement of the sealed test elements, for example, in the form of a disk which is subsequently referred to as the test element disk.

Moreover, the invention comprises individual test elements which are characterized in that a) they are provided with a tip or an edge which facilitates piercing of the sealing when the element is removed from its sealing, and/or b) they are provided with a notch which serves as a contact point for a mechanical unit, or c) they are provided with guiding elements which prevent a movement perpendicular to the main direction of movement during transportation parallel to the opposing sites in one of the rails receiving the guarding elements.

With the system in accordance with the invention, it is also possible to realize a method of analyzing sample liquids which is also covered by the invention. The method of analyzing sample liquids comprises the following steps:

Removing a test element from its sealing by means of a device

Transporting the test element to the site of sample application

Applying a sample onto the test element

Reading off the measurement.

In the method of analyzing sample liquids, a test element is preferably removed from a blister pack. To achieve this, a thorn is preferably used which is provided at a device and also serves the purpose of transporting the test element. The sample liquid is applied onto the reagent field of a test element that has been removed from its sealing. The measurement can be carried out with an above described measuring arrangement. In a preferred manner, the measurement is carried out at the side of the test element which is opposite the side of sample application.

In a system in accordance with the invention, several individually sealed test elements are provided within said system. In a preferred embodiment, the test elements are mechanically linked. A particularly advantageous arrangement of the test elements is a circular arrangement in the form of a disk which allows radial transportation of the chambers. Moreover, as the arrangement takes up only little space, a multitude of test elements can be accommodated in the instrument. The disk in accordance with the invention can be manufactured analogously to blister packs for tablets. Blisters are generally made of two foils, of which the first is provided with recesses into which the tablets or, in case of the invention the test elements, are inserted. A second foil is then attached to the first foil by means of sealing or gluing. The test elements are thus individually sealed and separated by means of spacers. The materials used for the foils are, for example, plastic materials. In accordance with the invention, however, plastic-laminated metal foils are preferred as they offer the better protection from moisture, light, and contamination. Particularly preferred are those foils where an aluminum layer is provided on a polyethylene layer, the aluminum layer being covered with an external lacquer. The individual test elements can principally be removed from the sealing by the user. However, in a preferred manner this is done by a mechanism and in a particularly preferred manner, this is a mechanism to perform both the removal of the test element from its sealing and the transport of the element to the site of measurement.

The test element disk can contain coded data referring to the contents of the disk, the expiration date of the test elements, the manufacturing lot, and other data. The coding can be realized by means of a barcode, a dot pattern, a magnetic strip, or other options known to the expert. The test element disk could also be supplied together with a code strip or a code key, e.g. in the form of a radio frequency identification key (RF-ID) containing the above-mentioned data. A reading device to read the respective form of data can be integrated into the system.

The data read by the test element disk can significantly improve handling of the instrument, for example, by warning if the stability of the test element has expired or by providing a lot-specific evaluation curve for the evaluation of the measurement.

BRIEF DESCRIPTION OF THE DRAWINGS

FIGS. 1 to 7 are examples illustrating a particularly preferred embodiment of the system wherein FIG. 1 is a complete measuring instrument with the inner and the outer covers being opened.

FIG. 3 is top view of an instrument base without the inner and outer covers and without the carrier for the test element disk.

FIG. 4 shows the bottom side of the inner cover.

FIG. 5 shows a test element disk

FIG. 6 shows an individual test element

FIG. 7 shows the bottom side of the outer cover with an additional test element disk.

DETAILED DESCRIPTION OF THE ILLUSTRATED EMBODIMENT

Figure 1:
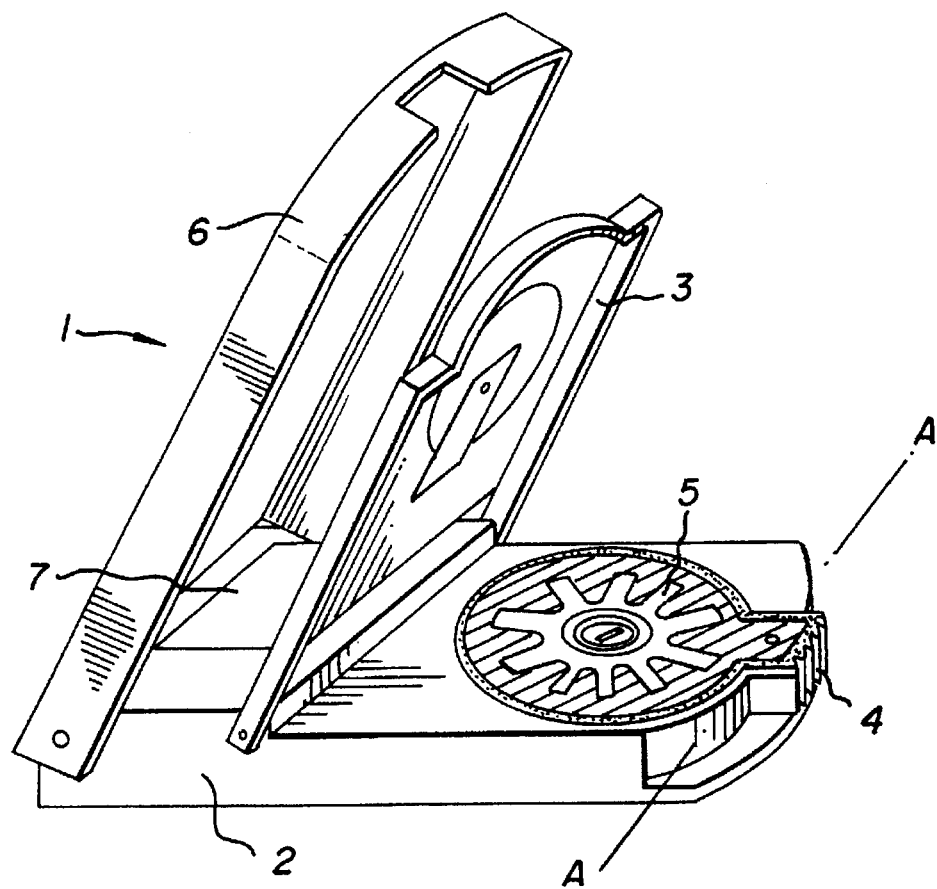
Figure 2C:
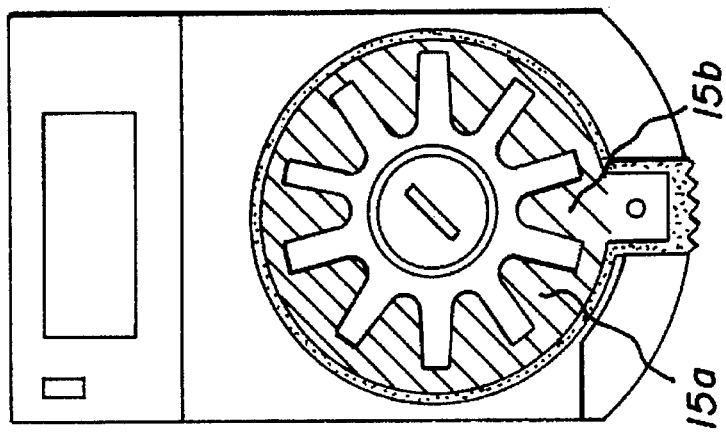
FIG. 2a–2c are top views of an instrument base with the inner and outer covers being removed.
Figure 2B:
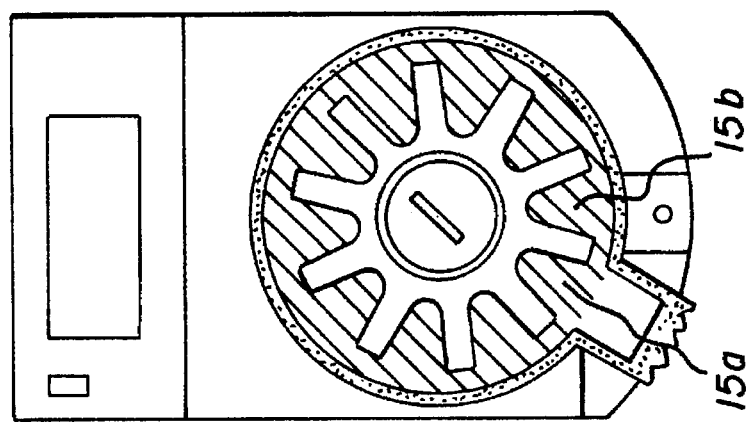
Figure 2A:
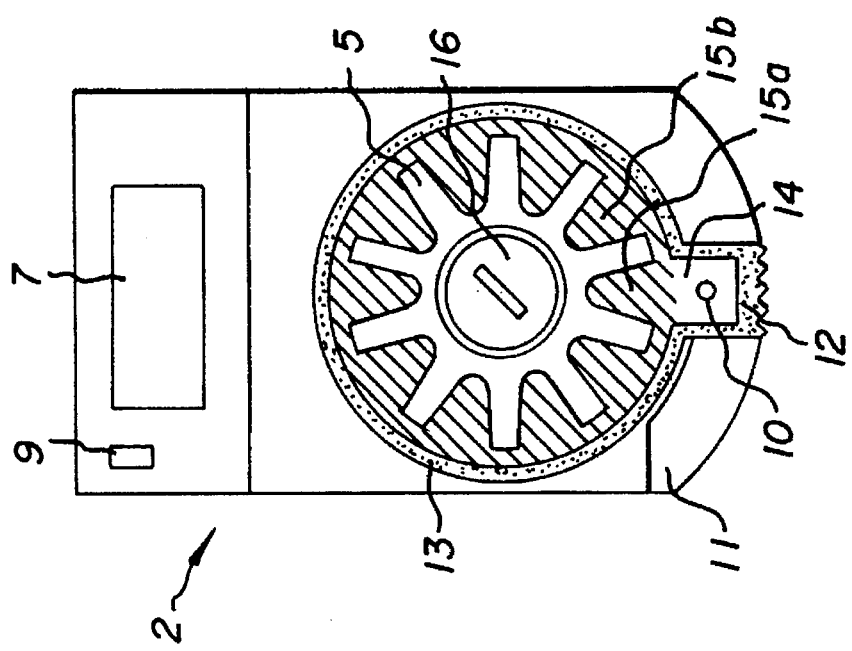
Figure 3:
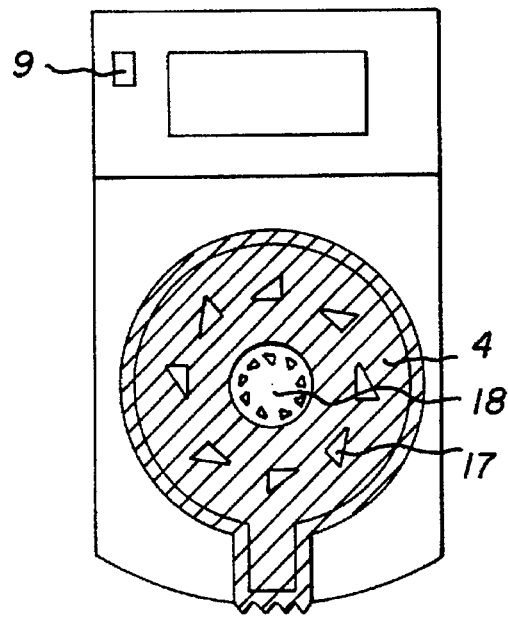

FIG. 1 shows an embodiment of the analysis system with a test element disk. A system in accordance with the invention belongs to those analysis systems where the analyte is applied onto a test element and evaluated in an instrument designed for this purpose. Test element and instrument are adjusted to each other with respect to shape and measuring signal so that their combination can be referred to as a system. The space in which the test element disk is inserted, is covered by an inner cover (3). The base (2) contains a first transport mechanism comprising a lever (4) and a rotatable support (5) for a test element disk. The outer cover (6) serves to protect the instrument from mechanical influences and to fix lever (4) in its position. Measurements are preferably carried out with the outer cover (6) being opened. It is, however, also possible to carry out a measurement with the outer cover (6) being closed which then provides an additional protection against the effects of ambient light. Closing the outer cover (6) is an additional protection of a device for displaying the measurement result, for which provision can be made if desired, against mechanical influences. FIG. 2 shows the base (2) of the instrument. On the one side of the lever (4) there is a recess (11) to move the lever radially into this direction while a movement into the opposite direction from the position shown in FIG. 2a is not possible. Lever (4) comprises a rectangular front part (12) and a circular disk (13). The rectangular front part of lever (12) has a cut-out (14). The sides of the cut-out (14) are formed to guide a test element if the latter is inserted into the cut-out. These guiding elements keep the test element in position during the measurement, but allow ejection of the test element once the measurement is completed. During the measurement, the test element is located within the cut-out (14) and the guiding element ensure proper positioning during the measurement. Below the cut-out (14), a measuring arrangement comprising a light source and a detector is integrated into the base (2). FIG. 2 shows a measuring opening (10) which allows light emitted from the light source and light reflected by the test element to pass. The light source can be present in mono- as well as polychromatic embodiments as they have already been described and are known in prior art. The detector can also be provided in different embodiments, preferred are detectors for the visible and the infra-red range of the spectrum. An electronic unit processes the signals in the base (2) in a known manner and the result is presented to the user in a comprehensible form on the display (7). The already described support (5) for the test element disk rests on the circular disk (13) of the lever. The support (5) is provided with recesses (15) to hold the sealed test elements (25), if a test element disk (22) has been placed on the support (5). The circular ring (13) of the lever, the support (5) for the test element disk and the base (2) of the instrument are rotatably connected to each other by means of a screw (16). If the screw (16) is removed, the support (5) can be withdrawn. The remaining arrangement of the base (2) with the lever (4) is shown in FIG. 3. The lever (4) is provided with ramps (17) allowing the support (5) to be rotated on the lever (4) in one direction, but preventing rotation in the opposite direction. An inner disk (18) is rigidly connected to the base (2). This inner disk (18) is also provided with small ramps having the same orientation as those on the lever (4). If, looking at the arrangement of FIG. 2a, a clock-wise movement of the lever is executed, support (5) is carried along in a clock-wise sense to cover the same angle which is covered by the lever. FIG. 2b shows the base of the instrument after execution of a maximally possible rotation. In the example which is a drawing of a disk that contains test elements, the lever covers an angle of 36°. Generally, an angle of 360°/n is possible for a disk with n test elements. If the lever is returned into the position shown in FIG. 2c in a counter-clock-wise sense, support (5) will remain in the position shown in FIG. 2b. Purpose of this mechanism is to use the movement of the lever to position a new test element of the test element disk in front of the cut-out (14) of the lever. The sequence of pictures shown in FIG. 2 demonstrates how the cut-out (15a), which is positioned in front of the detector in FIG. 2a, travels clock-wise to cover an angle of 36° and how a new cut-out (15b) is positioned in front of the detector. Together with support (5), lever (4) serves as a radial transportation mechanism.

Figure 4:
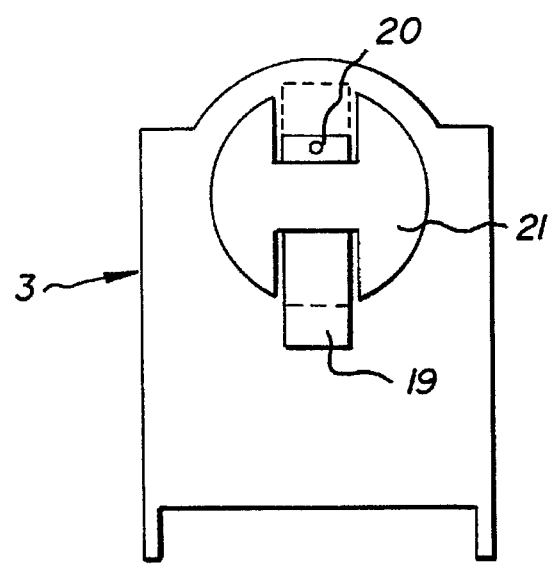

FIG. 4 shows the one side of the inner cover (3) of the instrument which faces the base (2). If the cover is closed, it is located horizontally above the base (2) and, hence, covers an inserted test element disk. In the inner cover (3), provision is made for a second transportation mechanism in the form of a pushing device (19) which carries a thorn (20) at its end. The position indicated by the continuous lines is the resting position of the pushing device (19). If the pushing device is moved to this position, lever (4) can be moved. If the pushing device (19) is in the position indicated by the broken lines, the end of the pushing device which carries thorn (20) is lowered toward the base (2). If a test element disk is inserted, the thorn (20) is lowered onto its surface to pierce it. Due to the continued movement of the pushing device toward the cut-out (14), the thorn pushes a test element into the cut-out (14) of the lever. During this movement, the test element also pierces the sealing around the test element disk. Once the above described operations have been executed, the test element is in the cut-out of lever (14) above detector (10). The sample can now be applied.

Figure 5:
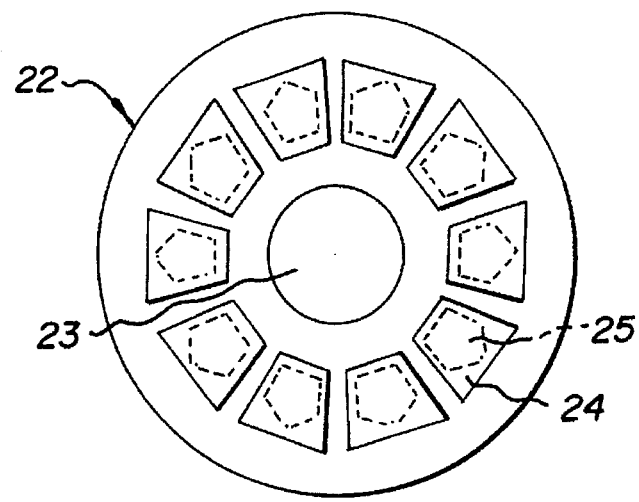

FIG. 5 shows a test element disk (22). In its center, it is provided with a circular cut-out (23) which comes to rest loosely on the mounting screw (16) when the disk is inserted into the instrument. The test element disk (22) is now fixed in its position such that only a rotation around the axis determined by the mounting screw is possible. The test element disk can be manufactured in the same way as described for the blister packs for tablets. The preferred materials for the test element disk include plastic-laminated metals as these are impermeable to moisture, with aluminum as a metal being particularly preferred. For less moisture-sensitive test elements, it is also possible to use plastics and cardboard.

The test elements are placed in cells (24) which are separated by spacers and sealed with respect to the surrounding so as to be protected from moisture, the effects of light, contamination, etc. The mechanical contact which allows transportation or rotation of the test element disk is realized via the cells (24) in the test element disk. Together with the test elements (25), the cells (24) form elevated portions with respect to the remaining test element disk (22). When the test element disk is inserted in the instrument, these elevated portions come to rest in the cut-outs (15) provided in support (5).

Figure 6:
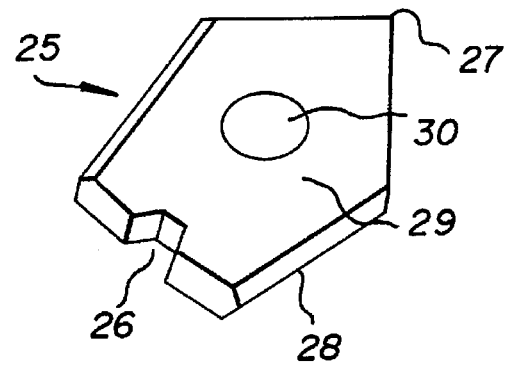

FIG. 6 shows an individual test element (25). The design of a test element in accordance with the invention which comprises a base (29) and a test field (30) has already been described. In a preferred embodiment, the base (29) is made of a plastic material and the test field (30) is also used as a measuring field. The measuring field at the lower side of the test element (25) is located above the measuring opening (10), if the whole unit has assumed proper position. In a preferred form, the test element is provided with a tip (27) to facilitate piercing of the cover foil of the test element disk when the latter is pushed out. At its other end, the test element is provided with an indentation (26) which the thorn (20) enters when the test element (25) is pushed out. This ensures proper guiding of the test element and prevents the thorn from slipping out of position. The lateral edges (28) of the test elements are made such that they fit in the lateral guiding elements of the cut-out (14) of the lever. This ensures proper guiding of the test element when the latter is inserted into its measuring position. The lateral edges (28) of the test element (25) can, for example, be configured as projecting edges. If the test element has been moved to the site of measurement, lever (4) can no longer be turned as the test element is arrested in its position by the thorn.

Figure 7:
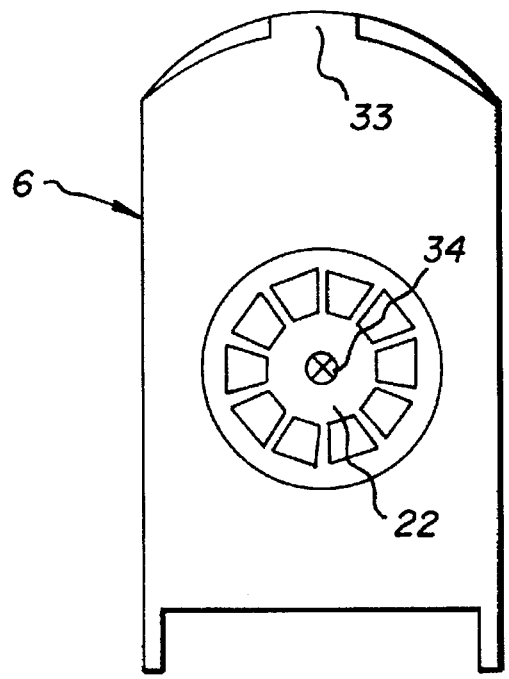

Lever (4) is also arrested in its position by the outer cover (6) shown in FIG. 7. A slot (33) in the front part of the cover extends over the projecting part of the lever (4) when said cover is closed. At its inside, the outer cover (6) can be provided with a mounting device (34) for another test element disk (22).

The base of the instrument can also have an integrated switching device (9) which is activated when the outer cover (6) is opened or closed. This signal can be used to switch the instrument on and off. In this preferred embodiment, the user does no longer have to manually turn the instrument on and off.

In the above described instrument, a measurement is carried out as follows:

1. Opening the outer cover (6) (instrument is automatically turned on).
2. Opening the inner cover (3).
3. Placing a test element disk onto support (5).
4. Closing the inner cover (3).
5. Releasing a test element by moving the pushing device (19) from its resting position (continuous lines in FIG. 4) to the position indicated by the broken lines. The test element is thus pushed from the test element disk into the cut-out (14) provided in lever (4).
6. Applying the sample onto the test element (measurement is started).
7. Reading the result off the display (7) once the measurement is completed.
8. Moving the pushing device (19) back into resting position.
9. Moving the lever from the position shown in FIG. 2a into the position shown in FIG. 2b. Once this movement is executed, the test element drops into the recess (11).
10. Moving the lever back into the position shown in FIG. 2c.
11. Ejecting a used test element from the instrument.
12. Closing the outer cover (6) unless a new analysis is to be carried out.

If a test element disk has already been inserted in the instrument, the measuring procedure only comprises steps 5 to 11.

To remove an empty test element disk, both covers (6) and (3) are opened and the disk is removed.

Steps 8 to 10 can be omitted if the pushing device (19) and the lever (4) are returned by means of springs.

Figure 8:
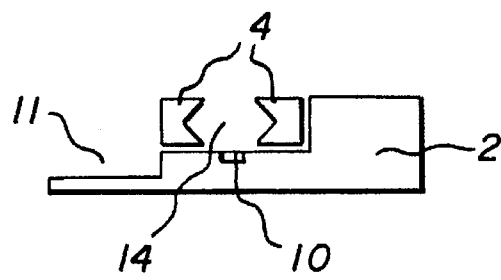
FIG. 8 is a cross sectional view of the instrument of FIG. 1, taken along line A—A.

FIG. 8 shows the recess (11) of the base (2) and how the lever (4) is located with respect to the measuring opening (10). The guiderails of the lever (4) are formed so that they can receive the test elements (25). The lateral edges (28) of the test elements fit into the guiderails of the lever (4).

The above described design is an example of how the instrument in accordance with the invention could be realized. A characteristic feature for a system of this kind is the presence of several individually sealed test elements inside the system and transportation of individual test elements from their sealed position to the site of measurement. An advantage of the system in accordance with the invention is that several tests can be carried out successively. The user does not have to manually take a new test element out of a separate container. In the present case, the determination can be carried out with one single instrument without requiring an additional container to store the test elements. Due to the individual sealing, the test element is particularly suited for use with test elements that are sensitive to environmental factors (e.g. humidity, oxygen in the air, light) as these test elements are protected by the individual sealing. If the measurement is carried out as described, erroneous usage by malpositioning of the test elements is avoided as the test elements are directly moved to the site of measurement by means of the described mechanism. Moreover, the ejection mechanism allows removal of used elements without contamination of the user.

| List of Reference Numerals |
| --- |
| 1 Instrument |
| 2 Base |
| 3 Inner cover |
| 4 Lever |
| 5 Rotatable support |
| 6 Outer cover |
| 7 Display |
| 9 Switching device |
| 10 Measuring opening |
| 11 Recess in base |
| 12 Rectangular front part of lever (4) |
| 13 Circular disk of lever (4) |
| 14 Cut-out in lever (4) |
| 15 Cut-out in support (5) for test element disk |
| 16 Screw |
| 17 Ramp |
| 18 Inner disk |
| 19 Pushing device |
| 20 Thorn |
| 21 Attachment for pushing device |
| 22 Test element disk |
| 23 Circular cut-out in the test element disk (22) |
| 24 Cell of test element disk (22) |
| 25 Test element |
| 26 Indentation of test element (25) |
| 27 Tip of test element |
| 28 Lateral edges of test element (25) |
| 29 Base of test element (25) |
| 30 Test field |
| 33 Slot in front part of the cover (6) |
| 34 Mounting device in outer cover (6) |

We claim:

1. An integrated array comprising a plurality of test elements, said test elements being radially arranged on a common plane, said integrated array also including a plurality of chambers therein, wherein each test element of the plurality of test elements is individually sealed in a chamber of said plurality of chambers, and wherein each test element includes a test field wherein detectable changes occur upon addition of sample liquids thereto, each test element including a piercing means thereupon for piercing a seal of the chamber when said each test element is pushed into contact with the seal.

2. An integrated array as recited in claim 1, wherein the seal is configured to be pierced by said piercing means of said each test element.

3. An integrated array as recited in claim 1, further including data means associated with the array which is specific for the test elements of the array.

4. An integrated array as recited in claim 1, wherein each of said plurality of test elements includes notch means thereupon, said notch means for contacting a transport mechanism, wherein said transport mechanism pushes said each test element out of the chamber.

5. An integrated array as recited in claim 1, wherein said each test element includes guiding means on opposing sides thereof, said guiding means for guiding said test element in a main direction of movement and for preventing movement perpendicular to the main direction of movement, when the test element is moved in the main direction.

6. An integrated array as recited in claim 5, wherein said guiding means has a shape which corresponds to guide rails, and is configured to be received in said guide rails.

7. An integrated array as recited in claim 1, wherein each of said plurality of chambers comprise two foils sealingly attached to each other.

8. An integrated array as recited in claim 7, wherein each of said two foils each comprise a plastic-laminated metal foil.

9. An integrated array as recited in claim 1, further comprising a circular aperture therein.

10. An integrated array as recited in claim 1, wherein said piercing means comprises a tip of said test element.

11. An integrated array as recited in claim 1, wherein said piercing means comprises an edge of said test element.

* * * * *